United States Patent [19]

Dastoli et al.

[11] Patent Number: 4,880,581
[45] Date of Patent: Nov. 14, 1989

[54] MEANS AND METHOD FOR ASEPTIC PARTICLE-FREE PRODUCTION OF ARTICLES

[75] Inventors: Frank R. Dastoli, Arlington; Bernard Z. Senkowski, Fort Worth; Dieter W. Wagener, Fort Worth; George H. Bogdanffy, Fort Worth; Gaurang R. Vin, Arlington, all of Tex.

[73] Assignee: Alcon Laboratories, Inc., Fort Worth, Tex.

[21] Appl. No.: 946,342

[22] Filed: Dec. 24, 1986

[51] Int. Cl.$^4$ .............. B29C 33/10; B29C 49/46; B29C 49/62; F24F 7/10
[52] U.S. Cl. .................. 264/39; 264/37; 264/238; 264/525; 425/74; 425/210; 425/225; 425/317; 425/446; 425/812; 425/815; 425/522; 425/542; 98/33.1; 98/31.5; 98/115.3; 55/385.2
[58] Field of Search ............ 264/37, 525, 39, 238; 425/210, 225, 522, 538, 542, 317, 342.1, 387.1, 446, 812, 815, 216.116, 73, 74; 55/279, 385 R, 385 A; 98/33.1, 31.5, 115.3

[56] References Cited

U.S. PATENT DOCUMENTS

| | | | |
|---|---|---|---|
| 3,423,495 | 1/1969 | Bachner | 264/96 |
| 3,523,329 | 8/1970 | Gallay | 18/5 |
| 3,597,516 | 8/1971 | Harwood | 264/96 |
| 3,643,586 | 2/1972 | Robinson | 99/234 R |
| 3,712,784 | 1/1973 | Siard et al. | 425/387 |
| 3,792,144 | 2/1974 | Burkett et al. | 264/96 |
| 3,809,768 | 5/1974 | Berry | 426/309 |
| 3,814,783 | 6/1974 | Dardaine et al. | 264/89 |
| 3,999,922 | 12/1976 | Shimada | 425/210 |
| 4,026,982 | 5/1977 | Dardaine et al. | 264/89 |
| 4,208,852 | 6/1980 | Pioch | 53/167 |
| 4,267,769 | 5/1981 | Davis et al. | 55/385 A |
| 4,336,015 | 6/1982 | Rainville | 425/210 |
| 4,342,184 | 8/1982 | Van Eck et al. | 53/452 |
| 4,401,423 | 8/1983 | Bellehache et al. | 264/525 |
| 4,510,115 | 4/1985 | Gokeen et al. | 264/525 |
| 4,660,464 | 4/1987 | Tanaka | 98/115.3 |
| 4,668,484 | 5/1987 | Elliott | 422/243 |

FOREIGN PATENT DOCUMENTS 3500175.5 7/1985 Fed. Rep. of Germany.

Primary Examiner—Jan H. Silbaugh
Assistant Examiner—Neil M. McCarthy
Attorney, Agent, or Firm—James A. Arno; Gregg C. Brown

[57] ABSTRACT

An apparatus and method for aseptic, particle-free production of articles. A shroud is placed around at least a portion of the device which produces the articles to substantially isolate that portion from the external environment. The device for producing the articles and the shroud are sterilized and the air inside the shroud is filtered and sterilized. A laminar or other type of flow of filtered, sterilized air is imparted through the shroud over the articles being produced. A secondary shroud encloses the corridor or work area adjacent the shroud and device which produces the articles. The corridor and secondary shroud are sterilized, and sterilized and filtered air is continually introduced therein. The articles therefore are particle-free and sterilized for further use. The apparatus and method can be used for any component production process employing high temperatures and/or pressures, including, but not limited to, blow molding, injection molding, and production of semiconductor electronic components. In the case of blow molding, sterilization of the interior of the article being blow molded is accomplished by blowing the article with filtered and sterilized air.

23 Claims, 3 Drawing Sheets

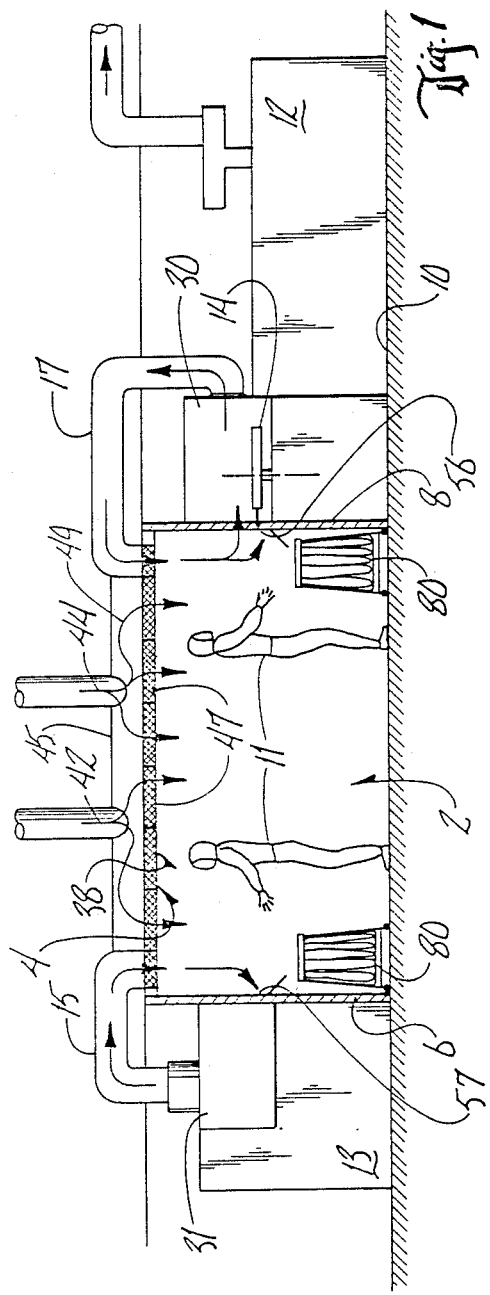
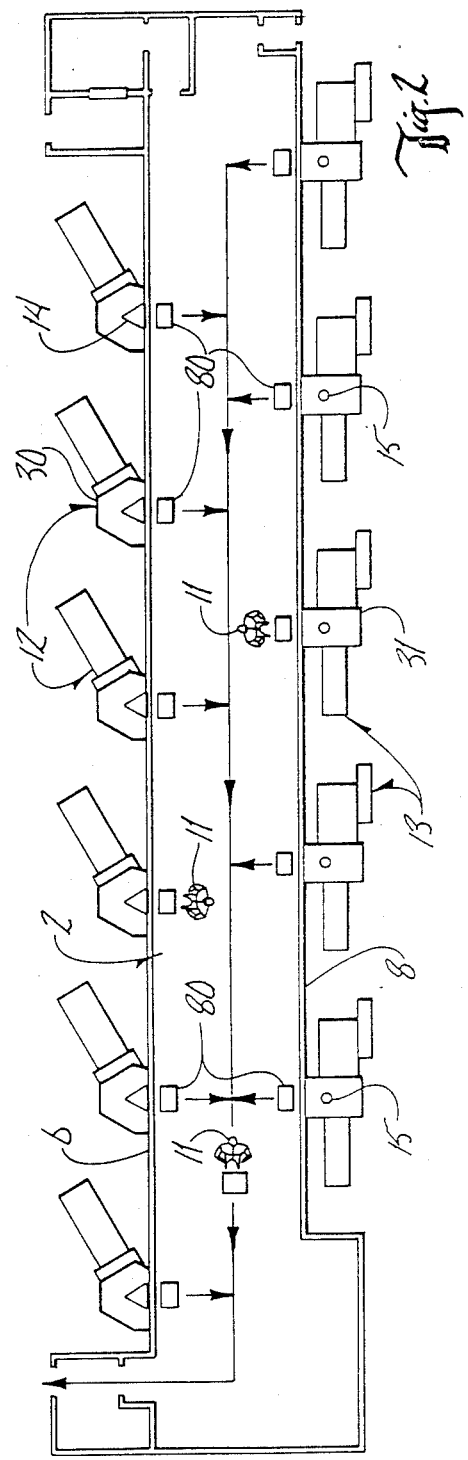

MEANS AND METHOD FOR ASEPTIC PARTICLE-FREE PRODUCTION OF ARTICLES

BACKGROUND OF THE INVENTION

1. Field of the Invention

The present invention relates to means and methods for aseptic, particle-free production of articles, and in particular, to means and methods for producing both externally and internally sterilized, particle-free articles which are manufactured under high temperature and/or high pressure.

2. Problems in the Art

There are many products which are desired to be, or out of necessity need to be, sterilized and particle-free. For example, the pharmaceutical and health care industries, of necessity, require aseptic instruments, containers, caps, plugs, and the like. Similarly, semiconductor electronic component production requires a particle-free and sterilized environment to ensure reliable and quality articles. Such need is well known within these arts. It is to be understood that the term "particle-free", as used herein, means "particle-reduced" or "particle-minimized", as it is virtually impossible to eliminate all foreign particles from a manufactured container.

In the case of containers for pharmaceuticals or other health care products, sterile conditions must exist not only for the interior of the container and caps, but also for the exterior of all portions of the container and caps prior to filling. Thus, it is critical that aseptic conditions exist in the manufacturing of the containers and caps to allow them to be sterile and particle-free when they are filled and sealed.

Conventionally, pharmaceutical or health care containers and caps were sterilized by imparting sterilizing gas, such as steam or EtO, onto the articles, or by applying gamma radiation to the articles. These conventional methods may be referred to as "secondary" sterilization methods, since the sterilization step is preformed subsequent to formation of the articles. While such procedures have proved adequately effective for sterilization in appropriate circumstances, they require additional and significant equipment, time, and cost over and above that needed for the manufacturing of the articles. Also, significant health risks and hazards accompany the use of EtO.

It is also known that in many applications, such as making pharmaceuticals or in laboratories, foreign particles may be minimized by using "clean-room" procedures. "Clean-room" procedures include sterilizing the surfaces involved in the process or processes taking place therein, filtering the air in the room, and having workers use sterilized gloves, lab coats, masks, hats, etc. Such procedures do not ensure sterility, but rather tend only to reduce contamination or enhance the probability of sterility. Additionally, such procedures reduce larger particle contamination, but may not be effective for the very smallest contaminating particles such as micro-organisms.

It is therefore a primary objective of the present invention to provide a means and method for aseptic, particle-free production of articles, which improves over or solves the problems and deficiencies in the art.

Another object of the invention is to provide a means and method as above described which eliminates conventional sterilization steps, equipment, costs, and handling while producing aseptic, particle-free articles.

A further object of the invention is to provide a means and method as above described which can provide a sterile environment for both production and handling of articles.

A further object of the present invention is to provide a means and method as above described which can produce internally and externally sterile and particle-free articles.

Another object of the present invention is to provide a means and method as above described which can be applied to the production of any type of component manufactured under high temperatures and/or pressures.

A further object of the invention is to provide a means and method as above described which can produce sterile and particle-free articles whether the articles be solid or have hollowed places or interior sections.

A further object of the invention is to provide a means and method as above described which eliminates or greatly reduces the use of chemicals or irradiation.

Another object of the present invention is to provide a means and method as above described which is economical, flexible in use, efficient, safe, and reliable.

A further object of the present invention is to provide a means and method as above described which may be retrofitted to existing production machines and techniques.

These and other objects, features, and advantages of the present invention will become more apparent with reference to accompanying specification and claims.

SUMMARY OF THE INVENTION

The present invention is a means and method for aseptic, particle-free production of articles or components. Traditionally, many articles are sterilized by using special equipment to impart gases, such as EtO and steam, or radiation, such as gamma radiation, upon the articles. The present invention eliminates the time, equipment, and cost of such steps by providing a method and apparatus for the production of articles that are both sterile and particle-free, thereby eliminating the necessity for sterilization subsequent to production of the articles.

At least a portion of the means or mechanism to produce the article is surrounded by and substantially isolated from the external environment by a primary shroud. Before production and handling, the primary shroud and means for producing the articles are sterilized by methods known in the art. Parts of the means for producing the articles can also be selectively modified to further enhance and maintain a sterile production environment. The air inside the primary shroud is filtered and sterilized, as is any air which enters within the primary shroud. A flow of filtered, sterilized air is imparted over the articles being produced to insure that no contaminating particles are allowed to adhere or settle upon the articles being produced. The flow is preferred to be a laminar flow, by the invention can function with other types of air flow.

A secondary shroud is placed surrounding and enclosing the corridor or work area adjacent to the primary shroud. The interior of the secondary shroud can also be sterilized according to known methods in the art. Only filtered, sterile air is allowed into the secondary shroud to maintain a "clean-room" environment. If a number of article-producing mechanisms are used, multiple primary shrouds with corresponding article-producing mechanisms can be positioned along the secondary shroud.

The means and method of the invention can be applied to many types of production techniques where high temperatures and/or pressures are employed. Examples include, but are not limited to, production of semiconductor electronic components, injection molding, and blow molding. In the instance of blow molding, to ensure sterilization of the inside of the article, the pressurized gas (usually air) used to blow mold the article is itself also filtered and sterilized.

By maintaining the primary shroud over a portion of each of the mechanisms for producing the articles, and by utilizing the secondary shroud over the corridor including discharge and handling portions for the articles, sterility and a particle-free environment can be maintained from production to bagging of the articles so that their sterility can be maintained for transport, filling, and sealing.

BRIEF DESCRIPTION OF THE DRAWINGS

FIG. 1 is a schematic elevational view of the invention as applied to blow and injection molding machines.

FIG. 2 is a schematic plan view of the positioning of multiple blow and injection molding machines along a clean-room corridor.

DETAILED DESCRIPTION OF THE PREFERRED EMBODIMENTS

Figure 3:
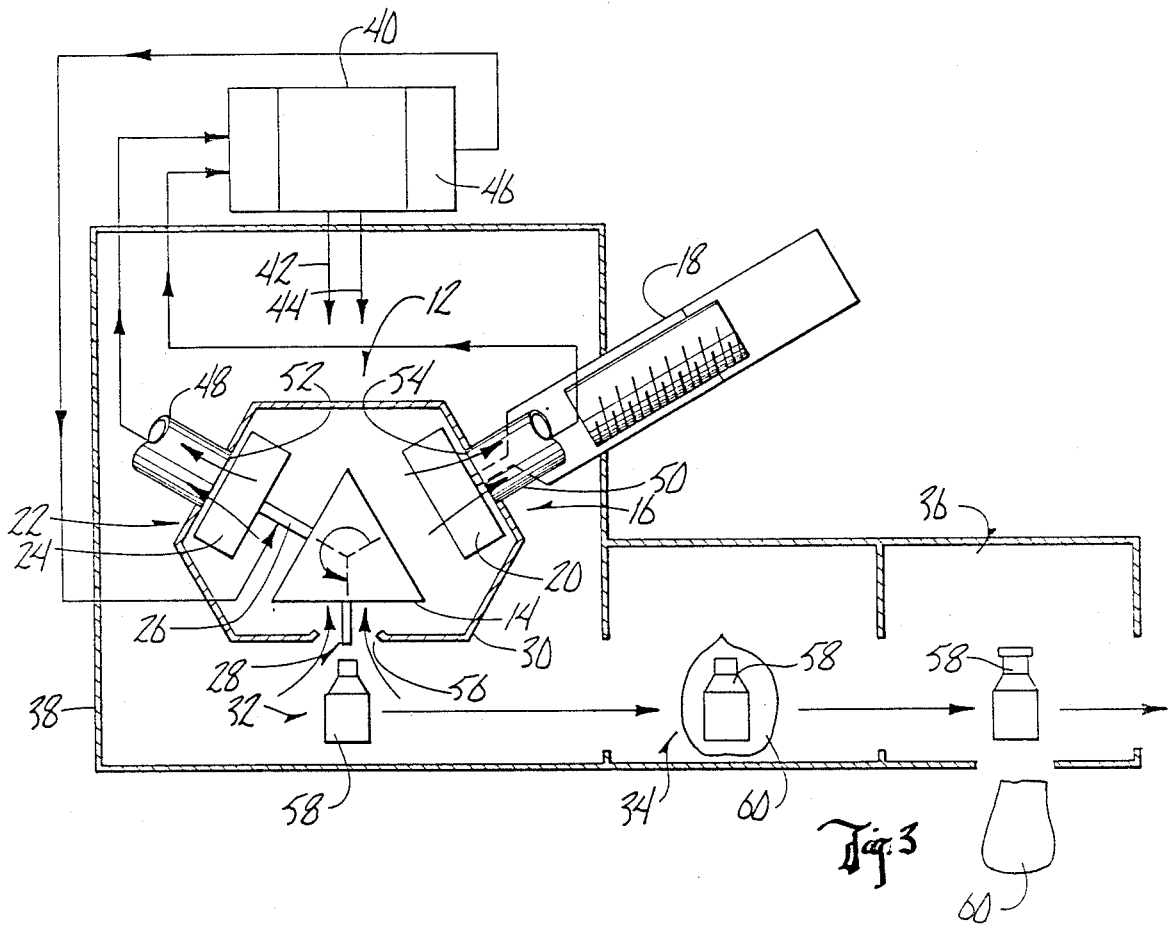
FIG. 3 is a schematic plan view of an embodiment of the invention shown applied to a single blow molding mechanism, additionally schematically depicting auxilliary and optional filler/debagger/capper stations.

To further describe the invention, preferred embodiments of the invention will be described and reference should be taken to the drawings. It is to be understood the description and drawings illustrate preferred embodiments of the invention only, and that the invention can take on a variety of forms, shapes, and methods, all within the scope of the invention. In particular, it is to be further understood that the present invention can be applied to conventional article-producing machines and processes, whereby selected modifications can be completed which can enhance, maintain, or improve the sterile production environment around the article-producing machines or processes. These selected modifications will be described in greater detail below. Alternative preferred embodiments will also be discussed.

By referring to FIGS. 1 and 2, the general configuration and operation of one preferred embodiment of the present invention can be seen. A long corridor 2 is defined by a ceiling 4, first and second sidewalls 6 and 8, and a floor 10. One or more article-producing machines are positioned along corridor 2 allowing workers 11 access to the machines but containing workers 11 within corridor 2. In FIGS. 1 and 2, there are shown a plurality of blow molding machines 12 and injection molding machines 13 spaced apart on opposite sides of corridor 2. It is to be understood that the present invention operates with respect to any plastic component manufacturing process which employs high temperatures and/or pressures. This includes injection and blow molding, but also includes other processes, such as are known to those of ordinary skill in the art.

By referring to FIG. 2, it can be seen that corridor 2 is isolated from the external environment by utilizing such things as air locks, air showers, and pass-through entrances/exits, which are used to help create and maintain an aseptic, particle-free or "clean room" environment within corridor 2. To accomplish these goals, workers 11 also wear sterilized gowns and and head gear equipped with a sterile filter (0.22 micron) and wash themselves before entering corridor 2.

According to the present invention, air is introduced into plenum 45 through conduits 42 and 44. Plenum 45 extends and covers the width of corridor 2. A plurality of absolute HEPA filters 47 are positioned between plenum 45 and corridor 2 to form a ceiling to corridor 2. Filtered and sterilized air is therefore introduced throughout corridor 2 through ceiling filters 47, as is shown by arrows 49. This filtered and sterilized air is then used to produce air flows over both the blow mold machines 12 and the injection mold machines 13. The air flows can be laminar air flows which can be produced by methods and structure well within the skill of those of ordinary skill in the art. One method is to pass the air through a perforated wall in the ceiling, in front of the machine, or in front of the exhaust duct or plenum.

A primary shroud 30 exists over each blow mold indexing head 14. Likewise, a primary shroud 31 surrounds each injection mold machine 13. Recirculation ducts or conduits 15 and 17 allow the filtered and sterile air pulled in from corridor 2 into shrouds 30 and 31 to be recirculated back through ceiling 4 and ceiling AEPA filters 47 back into corridor 2 adjacent to shrouds 30 and 31. A continuous recirculating laminar or other type of flow of sterilized and filtered air thus is produced over the blow molding and injection molding machines and processes to assist in achieving the objects of the invention. Each shroud 30 and 31 has a shroud window 56 or 57 respectively to allow entrance of sterilized, filtered air from corridor 2, and to allow discharge of blow molded or injection molded articles into sterilized double bags 80 for transport to filling and capping stations or other use.

It can thus be seen that the present invention combines "clean-room" technology with laminar or other types of air flow directly over the article-producing structure. Ceiling 4, sidewalls 6 and 8, and floor 10, defining corridor 2, can also be referred to as a secondary shroud 38, which isolates the corridor 2, workers 11 and the discharge areas occupied by bags 80 from the external non-sterile environment.

It is to be understood that the plasticization processes of blow and injection molding themselves have an inherent ability to sterilize the articles because of the high pressure and temperature utilized. Temperatures generally range between 170° to 230° Celsius, with pressures ranging up to 350 bar. The assurance of aseptic conditions, both interiorally and exteriorally of the articles, is improved by the present invention. It is believed that the greatest risk of contamination may come from the article-producing machines themselves, therefore, the laminar or other air flow is created from front-to-back of those machines, "front" meaning that part closest to the discharge area, and "back" meaning the opposite side. Any contaminating particles would then be carried into the recirculation conduits 15 and 17 where such contaminants would be filtered out. Also, this is why primary shrouds 30 and 31 cover only those parts of machines 12 and 13 as is necessary. The non-essential and "dirtier" parts of machines 12 and 13 are located outside of primary shrouds 30 and 31 and secondary shroud 38 to further reduce contamination risks.

FIG. 3 schematically and more particularly shows the general configuration and operation of another preferred embodiment of the present invention with respect to a conventional blow mold machine 12. The steps and structure of conventional blow molding are well-known in the art and are more thoroughly described in U.S. Pat. No. 4,336,015, which is herein incorporated by reference. With regard to the embodiment of the present invention as shown in FIG. 3, blow mold machine 12 has a rotating indexing head 14 which rotates within three stations. Injection station 16 includes an injection member 18 which takes plasticized material at high temperature and injects it into mold 20. The plastic material is extruded and injected into a parison mold to enable it to be molded around a core rod 26, and then the indexing head 14 rotates to the blow mold station 22 where sterile pressurized air is injected into the plastic material taken from mold 20. The plastic material is then placed within blow mold 24. Core rod 26 discharges pressurized, sterilized, and filtered air into the parison mold to "blow mold" it to its final shape. It is particularly pointed out that the pressurized gas (here air is preferred) to blow mold the parison is sterilized, filtered, and particle-free to maintain aseptic conditions in the interior of the article being blow molded.

After this step, the blow molded article on the core rod 26 is then rotated on the index head 14 to the stripper station 28 where it is discharged from indexing head 14 into secondary shroud 38 for further handling.

To insure aseptic conditions, shroud 30 is positioned so as to enclose only the indexing head 14 and stations 16, 22, and 28 of blow mold machine 12. Shoud 30 is preferred to be gas impermeable and in the preferred embodiment is made from plexiglas. Shroud 30 serves to substantially isolate the production portions of blow mold machine 12 from the external environment, including the external air and the rest of blow mold machine 12 itself. Secondary shroud 38 should also be gas impermeable and in the preferred embodiment can be composed of rigid walls and/or plastic curtains.

A filtered and sterilized air source 40 is put in fluid communication with the inside of secondary shroud 38 to maintain an input of filtered, particle-free, sterilized air within secondary shroud 38. This is depicted in FIG. 3 by arrows representing conduits 42 and 44.

Furthermore, pressurization means pulls air through two conduits 48 and 50 at generally opposite sides of the interior of shroud 30 through openings 52 and 54 in shroud 30. By referring to FIG. 3, it can be seen that conduits 48 and 50 are positioned so that the pressurized, sterilized air is pulled directly over injection station 16 and blow mold station 22. The sterile, pressurized air enters through shroud window 56 into primary shroud 30 from secondary shroud 38. Therefore, a laminar or other type of flow of sterilized, particle-free air is directly imparted upon the article 58 being produced at the stations of blow mold machine 12. This laminar or other type of flow prevents contaminating particles from adhering or settling upon article 58. The air is pulled from the front of the blow molding machine 12 (as defined generally by the window 56), to the back of the machine 12 generally opposite window 56. This assists in moving particles away from the discharge area around shroud window 56. The air is then filtered in sterilized air source 40 before being recirculated back into secondary shroud 38.

Article 58 is also discharged out of shroud window 56 after it is blow molded. It is then transported by means known within the art to successive stations. FIG. 3 shows, schematically, bagging station 34, where sterilized blow molded articles are put into sterilized bags. FIG. 3 also shows, for example only, that after bagging, articles 58 might be directly transported by means known in the art to debagger, filler, and capper stations. Aseptic conditions could be maintained by enclosing such stations in a secondary shroud. However, it is to be understood that the debagging, filtering, and capping stations do not form a part of the present invention. The methods of the present invention could be applied to them, however. The articles are filled, sealed by a cap, and the bags are disposed of at the filler/debagger/capper stations 36. The product at this point is ready for shipment. Because secondary shroud 38 substantially isolates the articles from exterior environment and air, and is filled with sterilized and filtered air, the aseptic environment for article 58 can be maintained to the end product.

It is particularly pointed out that the present invention maintains sterility of articles 58, both interiorally and exteriorally. This is crucial to maintain a totally aseptic environment.

It is also to be understood that the same procedures can be utilized for other article producing processes, such as injection molding, semiconductor electronic component production, or any other plastic component manufacturing process employing high temperature and/or pressure. Just as with FIG. 3, such procedures would be accomplished in an aseptic environment by putting shroud 30 around at least a portion of the production machine, imparting laminar or other flow of sterilized, filtered, particle-free air upon the articles 58 as they are being produced, and maintaining a sterilized, particle-free, environment in the work area adjacent to the production machine.

Figure 4:
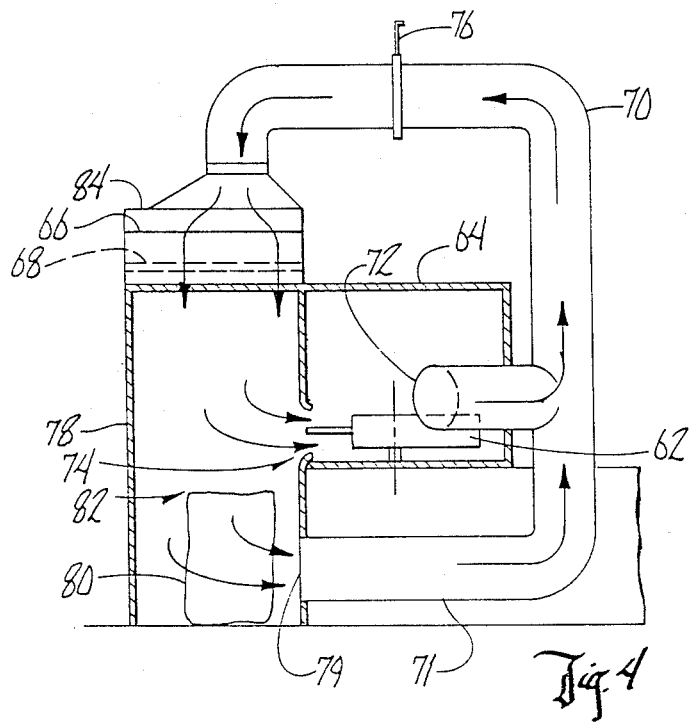
FIG. 4 is an elevational schematic view of the general invention of FIG. 3 showing further optional features.

FIG. 4 shows another embodiment for carrying out the present invention. A portion of article production machine 62 is placed within primary shroud 64. A fan 66 having a filter 68 would produce filtered, pressurized air which would be sent out from plenum 84 into secondary shroud 78. The negative pressure behind fan 66 in recirculation conduits 70 and 71 causes sterilized, filtered air from secondary shroud 78 to be pulled through primary shroud window 74 and secondary shroud window 79 for refiltering and recirculation. The air pulled through recirculation conduit 70 by entering opening 72 in primary shroud 64 is drawn across article production machine 62 away from primary shroud window 74. A laminar or other type of flow of pressurized, sterilized and filtered air would then be set up in primary shroud 64 over the articles being produced. A blast gate 76 is imposed in the air conduit 70 to adjust the velocity of the recirculated air and the laminar or other air flow. The secondary shroud 78 is shown surrrounding window 74 and the inlet to fan 66. It also surrrounds sterilized bag 80 and discharge area 82 to maintain as aseptic environment for the articles.

Alternatively, similarly to conduits 48 and 50 of FIG. 3, more than one conduit 70 could be placed within primary shroud 64 to present a plurality of air flow outlets from shroud 64.

Figure 5:
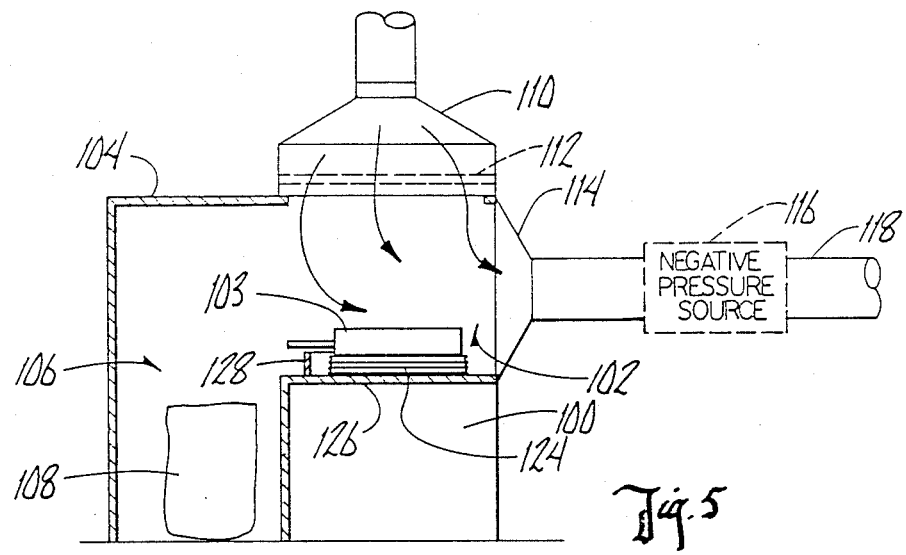
FIG. 5 is an elevational schematic view of an alternative embodiment of the invention.

FIG. 5 shows still another enbodiment of the invention. The article-producing machine, in this case a blow molding machine 100, again has a primary shroud 102 enclosing, at least substantially, the indexing head 103 of blow molding machine 100. A secondary shroud 104 encloses the discharge area 106 adjacent to blow molding machine 100. Collection bag 108 is shown as a receptacle for blow molded items. It can therefore be seen that most of blow molding machine 100 is segregated outside of primary and secondary shrouds 102 and 104. In this embodiment, filtered and sterilized air is introduced at relatively low velocity (for example 20 to 30 feet per minute) through an air inlet plenum 110. Plenum 110 extends generally across the width of primary shroud 102 and has an absolute HEPA filter 112 across its periphery.

An air outlet plenum 114 is positioned generally across a large portion of the side of the primary shroud opposite the discharge area or station and presents an exhaust for the incoming filtered and sterilized air through plenum 110. Outlet plenum 114 always will represent an area of negative pressure to pull in the air from plenum 110. The necessary air flow across indexing head 103 is therefore accomplished.

Optionally, a negative pressure source 116 can be operatively included along the exhaust conduit 118 behind exhaust plenum 114 to further enhance exhaust. Negative pressure source 116 could be a vaccum source, such as in known within the art.

Low velocity input air flow is preferred in this embodiment to eliminate or reduce turbulence around indexing head 103 which might be caused by higher velocity air flows. Depending on the type of negative pressure used in the exhaust outlet, exhaust velocity can be increased from inlet velocity, sometimes up to 200 feet per minute.

Figure 6:
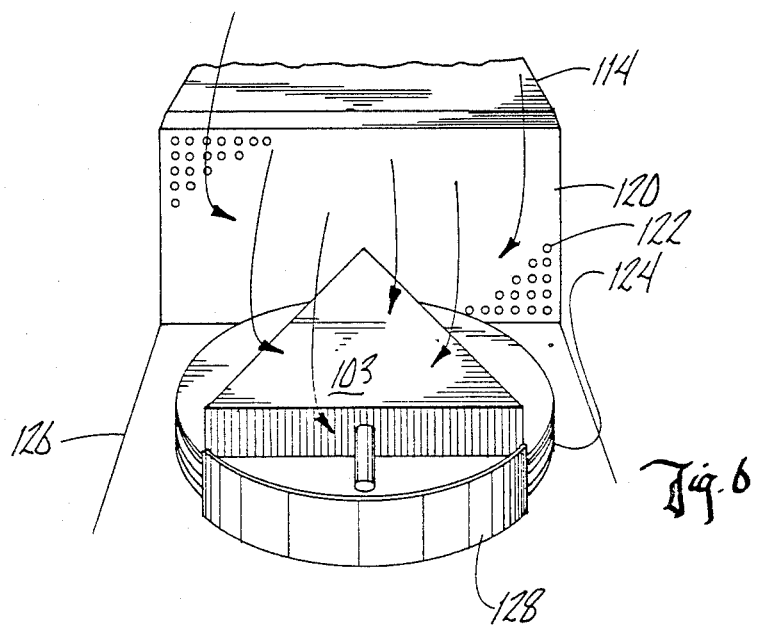
FIG. 6 schematically depicts, in perspective, optional features for the embodiment of FIG. 5.

FIG. 6 shows optional features which can be added to the embodiment of FIG. 5, and any other relevant embodiment, to further enhance the invention. First, a perforated wall 120 is shown across the opening to exhaust air plenum 114. Perforations 122 assist in setting up air flow across the entire cavity defined by the primary shroud 102 to assure that sterilized and filtered air captures and transports particles generated from machine components. Such an air flow is a type of laminar flow.

Secondly, it is to be understood and is known by those of ordinary skill in the art, that indexing turrent or head 103, in addition to rotating, moves up and down very quickly from time to time during its operation. Such movement can cause turbulence or disadvantageous air flows. A skirt 124 can optionally be attached around the perimeter of head 103 and extend down to table 126. As shown in FIG. 6, skirt 124 can be in the shape of an expansible bellows to allow expansion and contraction in accordance with the raising and lowering head 103. A second optional barrier or skirt 128 can be positioned between indexing head 103 and discharge area 106. Skirt 128 is preferred to be closely adjacent to indexing head 103 and extend in an arc of about 120° across the front of head 103 as it faces the discharge area.

Skirts 124 and 128 channel compressed air from the moving and reciprocating head 103 to the rear of the machine into exhaust plenum 114, again assisting in removing particles generated from the various mechanical parts out of primary shroud 102.

It is to be further understood that the invention also consists of optional selective modifications to the components of the article producing machines, and the other elements described with respect to the invention to further enhance, improve, and maintain a sterile operational environment. Some of these modifications also enhance the safety or operational efficiency of the invention.

The primary shrouds, which can also be called guard cages, not only isolate the article-producing portions of the article-producing machines, and direct air flow over them, but also protect workers and operators from the equipment. To allow access to the indexing head or other equipment, it must be raised and lowered on guideposts. To minimize possible particle contamination, the primary shrouds can be modified to locate the guideposts on their outside periphery.

All coolant and heating lines can be routed through bulkhead fittings in the machine table to eliminate multiple hoses. Any braided hoses can be covered with neoprene.

Further modifications to the primary shrouds or guard cages include locating a polycarbonate material such as LEXAN ® [registered trademark of General Electric Company] on the interior of the primary shroud. Any framework or other structural supports can be located on the outside thereof. Corners can be gusseted for required strength. Such things as latches and other hardware associated with the guard cages should be made of suitable sterilizable materials and, to the greatest extent possible, all corners or non-smooth areas should be eliminated.

Any gaskets should be made of materials such as Buna N, and not sponge. They should be fastened with glue or epoxy. Optionally, a hole can be drilled in the machine table. By coupling an exhaust hose to the hole, air can be exhausted from selected areas by creating negative pressure in the hose.

Bushings and washers can be made of plastic, and any parts requiring lubrication should have wiping elements associated with them. Threads and slots should be minimized. Any exposed threads should have a plastic thread protector sealed with silicon, or be covered with shrink tubing or teflon tape.

Materials such as nickel plated low carbon steel and low carbon stainless steel should be used in selected and specially sensitive areas. Very importantly, gaskets of appropriate materials such as Buna N should be used to isolate elements in the primary shroud. Wherever possible, elements should be relocated outside of the primary shroud to reduce required access inside. The rotating head should be modified to eliminate all unnecessary holes and fittings. All molds should be stainless steel except the blow mold which should be of Beriliam copper. The die set should be nickel plated.

Compressed air tubing should be 316L stainless steel rated for 150 lbs. of saturated steam pressure with a bleed valve as defined by the manufacturer. The compressed air lines throughout the machine should be sterilized with clean steam to assure that the air used in bottle blowing, cooling, and discharge of the bottles from the core rod at the end of the cycle is always sterile. The entire air tube system should be modified to facilitate use of the steam. Appropriate means should be included to drain condensate from critical points and the air in the system should have a low dew point range of −40° to −80° Fahrenheit to dry out the system.

Sterile air at low temperature and low dew point should be used to discharge the bottle from the core rod and at the same time pressurize the bottle with cold air to guard against contaminants entering the bottle during the cool down process after discharge from the core rod. Right after discharge from the core rod, the bottom surface of the bottle has a temperature range of 140° to 160° Fahrenheit. Air pressure into the bottle will prevent hot expanded air from collapsing, thereby creating a vaccum.

These steps will be appreciated and well within the understanding of those of ordinary skill in the art. Such modifications and procedures can be used and apply equally to all types of means and methods applicable to the present invention.

It will be appreciated that the present invention can take many forms and embodiments. The true essence and spirit of this invention are defined in the appended claims, and it is not intended that the embodiments of the invention presented herein should limit the scope thereof.

What is claimed is:

1. A method of aseptic, particle-free production of interiors and exteriors of articles, to avoid the need for chemical or irradiation treatment of the articles, and to provide aseptic articles which are prepared for further processing, comprising the steps of:
    creating an aseptic environment within a clean room;
    shrouding at least a portion of an article producing means of a production machine to substantially segregate the portion of the article producing means from the clean room but retaining some communication with the clean room;
    substantially isolating the portion of the article producing means which is shrouded from any external environment and from the clean room;
    sterilizing the interior of the clean room, the portion of the article producing means within the shroud, the interior of the shroud, and any surfaces of the shroud inside and communicating with the clean room;
    filtering and sterilizing any air enclosed by the clean room and the shroud; and
    imparting a flow of filtered, sterilized air through the clean room and into the shroud, over and around the articles being produced on the portion of the article producing means within the shroud, and out of the shroud, so that the articles produced will be aseptic interiorially and exteriorially and ready for further processing.

2. The method of claim 1 wherein the production machine for producing the articles comprises a blow molding machine which is located outside and adjacent to said clean air room.

3. The method of claim 2 comprising the further step of blow molding the articles by injecting filtered, sterilized air into the article being blow molded.

4. The method of claim 1 wherein the flow of filtered, sterilized air is a laminar flow.

5. The method of claim 1 wherein the production machine for producing the articles comprises an injection molding machine which is located outside and adjacent to said clean air room.

6. The method of claim 1 wherein the production machine for producing the articles comprises an electrical semiconductor component producing machine which is located outside and adjacent to said clean air room.

7. A method for aseptic, particle-free blow molding of interiorially and exteriorially sterile articles comprising the steps of:
    shrouding a portion of an article producing means of a production machine for blow molding sterile articles to substantially isolate the article producing portion of the blow molding machine from the remainder of the machine and from any external environment;
    sterilizing the portion of the article producing means of the blow molding machine and the machine shroud;
    filtering and sterilizing the air entered into the machine shroud;
    shrouding the work area adjacent to the shrouded portion of the article producing machine;
    sterilizing the work area and the shroud enclosing the work area;
    filtering and sterilizing the air entering the work area shroud;
    imparting a laminar flow of filtered, sterilized air over and around the articles being blow molded; and
    exhausting the laminar flow of filtered, sterilized air from the machine shroud;
    blowing filtered, sterilized air into the articles being blow molded.

8. An apparatus for aseptic, particle-free production of interiors and exteriors of articles comprising:
    a clean room having an aseptic environment;
    a production machine including a means for producing the articles, at least a portion of said article producing means being sterilized, said article producing portion of the machine being adjacent said clean room;
    a shroud substantially isolating the article producing portion of the machine from the remainder of the machine and from any external wnvironment, the shroud being sterilized;
    an inlet opening in the shroud communicating between the clean room and the shroud;
    means for filtering and sterilizing air entering the clean room and the shroud;
    means for imparting a laminar flow of filtered, sterilized air over and around the articles being produced;
    at least one outlet opening in the shroud for exhausting the laminar flow of filtered, sterilized air from the shroud.

9. The apparatus of claim 8 wherein the machine for producing articles comprises a blow molding machine located outside and adjacent to said clean room.

10. The apparatus fo claim 9 wherein the blow molding machine includes means for presenting filtered, sterilized air to blow mold the articles located outside and adjacent to said clean room.

11. The apparatus of claim 8 wherein all surfaces of the portion of the article producing means and the shroud are smooth and sterilized located outside and adjacent to said clean room.

12. The apparatus of claim 9 wherein the blow molding machine injects, extrudes, blows, and discharges the articles being produced.

13. The apparatus of claim 8 wherein the means for filtering and sterilizing the air and for imparting a laminar flow of filtered, sterilized air includes microfilters.

14. The apparatus of claim 8 wherein said means for laminar flow of filtered, sterilized air includes fans, adjustable air flow rate gates, and conduits.

15. The apparatus of claim 8 further comprising means to recirculate filtered, sterilized air.

16. The apparatus of claim 8 further comprising discharge and transport means for the articles being produced, said laminar flow of filtered, sterilized air also being directed on the discharge and transporting means.

17. The apparatus of claim 8 wherein said machine for producing the articles is an injection molding machine located outside and adjacent to said clean room.

18. The apparatus of claim 8 wherein said machine for producing the articles is a semiconductor electronic component producing machine located outside and adjacent to said clean room.

19. The apparatus of claim 8 wherein the outlet opening comprises a perforated wall having a plurality of openings dispersed over the wall to enhance laminar flow of air.

20. The apparatus of claim 8 further comprising a negative pressure means in communication with the outlet opening to enhance laminar flow over and around the articles being produced by the machine.

21. The apparatus of claim 8 further comprising a turbulence barrier means located between the inlet opening in the shroud and the portion of the article producing means to reduce turbulence caused by the portion of the article producing means in the shroud and to direct turbulence away from the inlet opening.

22. The apparatus of claim 8 further comprising turbulence barrier means located in the path of the laminar flow of the filtered, sterilized air between the inlet opening and the outlet opening of the shroud.

23. The apparatus of claim 8 further comprising turbulence barrier means associated with the portion of the article producing means of the production means to reduce turbulence caused by movement of the portion of the article producing means.

* * * * *